(12) United States Patent
Despeyroux et al.

(10) Patent No.: US 7,968,534 B2
(45) Date of Patent: Jun. 28, 2011

(54) SULFONAMIDE DERIVATIVES, PREPARATION THEREOF AND USE THEREOF AS ANTAGONISTS OF OREXIN 2 RECEPTORS

(75) Inventors: Pierre Despeyroux, Antony (FR); Evelyne Fontaine, Antony (FR); Gilles Courtemanche, Antony (FR); Pierrick Rochard, Antony (FR); Claudine Serradeil-Le Gal, Antony (FR)

(73) Assignee: Sanofi-Aventis, Paris (FR)

( * ) Notice: Subject to any disclaimer, the term of this patent is extended or adjusted under 35 U.S.C. 154(b) by 121 days.

(21) Appl. No.: 12/176,753

(22) Filed: Jul. 21, 2008

(65) Prior Publication Data
US 2009/0042851 A1 Feb. 12, 2009

Related U.S. Application Data

(63) Continuation of application No. PCT/FR2007/000119, filed on Jan. 22, 2007.

(30) Foreign Application Priority Data

Jan. 27, 2006 (FR) .................... 06 00755

(51) Int. Cl.
*A61K 31/135* (2006.01)
*A61K 31/397* (2006.01)
*A61K 31/40* (2006.01)
*A61K 31/445* (2006.01)
*C07D 295/027* (2006.01)
*C07D 205/04* (2006.01)
*C07D 211/56* (2006.01)
*C07C 311/21* (2006.01)

(52) U.S. Cl. .................. 514/210.01; 514/329; 514/422; 514/602; 546/223; 548/557; 548/953; 564/92

(58) Field of Classification Search ................... 548/557
See application file for complete search history.

(56) References Cited

FOREIGN PATENT DOCUMENTS

| WO | WO 01/81308 | 11/2001 |
|---|---|---|
| WO | WO 2004/033418 | 4/2004 |
| WO | WO 2004/041807 | 5/2004 |
| WO | WO 2006/024779 | 3/2006 |

OTHER PUBLICATIONS

Vippagunta, et al. Advanced Drug Delivery Reviews 48 (2001) 3-26.*
Document No. 149:53987, retrieved from CAPLUS on Aug. 23, 2010.*
4-Chloro-N-(1-Methylpiperidin-4-yl)-N-[1-(2-Phenylethyl)Piperidin-4-yl]Benzenesulfonamide, Peakdale Screening Library, Database Chemcats [Online] abstract, (2006).

* cited by examiner

*Primary Examiner* — Shawquia Young
(74) *Attorney, Agent, or Firm* — Jiang Lin

(57) ABSTRACT

The present invention is directed to a compound of formula (I):

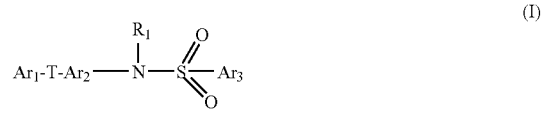

wherein $Ar_1$, $Ar_2$, $Ar_3$, R1 and T are as defined herein, its preparation, pharmaceutical composition and uses as orexin 2 receptor antagonist.

14 Claims, No Drawings

SULFONAMIDE DERIVATIVES, PREPARATION THEREOF AND USE THEREOF AS ANTAGONISTS OF OREXIN 2 RECEPTORS

This application is a Continuation of International Application No. PCT/FR2007/000119, filed Jan. 22, 2007, which is incorporated herein by reference in its entirety.

FIELD OF THE INVENTION

The subject of the present invention is sulfonamide derivatives, their method of preparation and their therapeutic use.

BACKGROUND OF THE INVENTION

Orexins A and B (or hypocretins 1 and 2) are hypothalamic neuropeptides of 33 and 28 amino acids respectively, that were recently identified as endogenous ligands of two receptors having seven transmembrane domains, named orexin 1 and orexin 2 receptors (Sakurai T., Cell, Vol. 92, 573-585, 1998; De Lecea L., Proc. Natl. Acad. Sci., Vol. 95, 322-327, 1998).

The orexin 2 receptor has the property of recognizing the two forms of orexin A and B in an equivalent manner. On the other hand, the orexin 1 receptor, which exhibits 64% homology with the orexin 2 receptor, is more selective and binds orexin A ten times better than orexin B (Sakurai T., Cell, Vol. 92, 573-585, 1998).

Via these receptors, orexins control various central and peripheral functions, in particular food and drink intake, certain cardiovascular endocrine functions and the wake/sleep cycle (Sakurai T., Regulatory Peptides, Vol. 85, 25-30, 1999).

It has now been found that some sulfonamide derivatives have a high affinity for the orexin 2 receptors and are potent antagonists of these receptors.

SUMMARY OF THE INVENTION

Accordingly, the subject of the present invention is compounds corresponding to general formula (I)

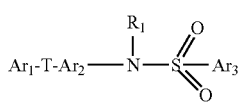

in which

Ar$_1$ represents an aryl group, optionally substituted with one or more groups chosen independently of each other from the following groups: a halogen atom, a (C$_1$-C$_4$)alkyl group and a (C$_1$-C$_4$)alkoxy group;

a heterocyclyl group, optionally substituted with one or more groups chosen independently of each other from the following groups: a halogen atom, a (C$_1$-C$_4$)alkyl group and a (C$_1$-C$_4$)alkoxy group;

T represents a group —(CH$_2$)$_n$— with n=0, 1, 2;

a group:

in which R is a hydroxyl group;

Ar$_2$ represents an aryl group, optionally substituted with one or more groups chosen independently of each other from the following groups: a halogen atom, a (C$_1$-C$_4$) alkyl group and a (C$_1$-C$_4$)alkoxy group;

a heterocyclyl group, optionally substituted with one or more groups chosen independently of each other from the following groups: a halogen atom, a (C$_1$-C$_4$)alkyl group and a (C$_1$-C$_4$)alkoxy group;

Ar$_3$ represents an aryl group, optionally substituted with one or more groups chosen independently of each other from the following groups: a halogen atom, a hydroxyl group, a (C$_1$-C$_4$)alkyl group and a (C$_1$-C$_4$)alkoxy group;

a heterocyclyl group, optionally substituted with one or more groups chosen independently of each other from the following groups: a hydroxyl group, a (C$_1$-C$_4$)alkyl group and a (C$_1$-C$_4$)alkoxy group;

R$_1$ represents a saturated heterocyclyl group of formula (A) which follows:

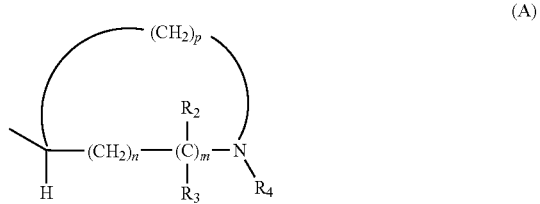

in which:

R$_2$ and R$_3$ represent independently of each other a hydrogen atom, a C$_1$-C$_3$ alkyl group; or alternatively R$_2$ and R$_3$ form together an oxo group;

R$_4$ represents a hydrogen atom or a C$_1$-C$_3$ alkyl group;

n=0 or 1; m=0 or 1; p=1 or 2;

provided that m and n never represent the value 0 at the same time;

or alternatively R$_1$ represents a cycloalkyl group of formula (B) which follows:

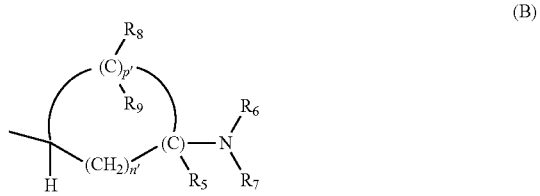

in which:

R$_5$, R$_6$ and R$_7$ represent independently of each other a hydrogen atom or a C$_1$-C$_3$ alkyl group;

R$_8$ and R$_9$ represent independently of each other a hydrogen atom or a C$_1$-C$_3$ alkyl group;

or alternatively R$_8$ and R$_9$ form together an oxo group;

n'=0, 1 or 2; p'=1, 2, 3 or 4;

DETAILED DESCRIPTION OF THE INVENTION

Among the compounds which are the subject of the invention, there may be mentioned a first group of compounds of general formula (I), in which $Ar_1$ represents
an aryl group, in particular a phenyl, optionally substituted with one or more groups chosen independently of each other from the following groups: a halogen atom, a $(C_1\text{-}C_4)$alkyl group and a $(C_1\text{-}C_4)$alkoxy group;
a heterocyclyl group, in particular pyridinyl or pyrimidinyl, said heterocyclyl group being optionally substituted with one or more groups chosen independently of each other from the following groups: a halogen atom, a $(C_1\text{-}C_4)$alkyl group and a $(C_1\text{-}C_4)$alkoxy group;

T represents
a group —$(CH_2)_n$— with n=1;

$Ar_2$ represents
an aryl group, in particular a phenyl, optionally substituted with one or more groups chosen independently of each other from the following groups: a halogen atom, a $(C_1\text{-}C_4)$alkyl group and a $(C_1\text{-}C_4)$alkoxy group;
a heterocyclyl group, in particular pyridinyl, optionally substituted with one or more groups chosen independently of each other from the following groups: a halogen atom, a $(C_1\text{-}C_4)$alkyl group and a $(C_1\text{-}C_4)$alkoxy group;

$Ar_3$ represents
an aryl group, in particular a phenyl, optionally substituted with one or more groups chosen independently of each other from the following groups: a halogen atom, a hydroxyl group, a $(C_1\text{-}C_4)$alkyl group and a $(C_1\text{-}C_4)$alkoxy group;
a heterocyclyl group, in particular pyridinyl, furanyl or pyrazolyl, optionally substituted with one or more groups chosen independently of each other from the following groups: a hydroxyl group, a $(C_1\text{-}C_4)$alkyl group and a $(C_1\text{-}C_4)$alkoxy group;

$R_1$ represents a saturated heterocyclyl group of formula (A) in which:
$R_2$, $R_3$ and $R_4$ each represent a hydrogen atom or a $(C_1\text{-}C_4)$ alkyl group;
p=2; m=n=1; or
m=0; n=1; p=2; or
m=0; n=p=1; or
m=n=p=1;
or alternatively $R_1$ represents a cycloalkyl group of formula (B) in which:
$R_5$, $R_6$ and $R_7$ represent independently of each other a hydrogen atom or a $C_1\text{-}C_3$ alkyl group;
$R_8$ and $R_9$ represent independently of each other a hydrogen atom or a $C_1\text{-}C_3$ alkyl group;
n'=0 or 1; p'=1, 2 or 3; in the form of a base, an addition salt with an acid, a hydrate or a solvate, in the form of enantiomers, diastereoisomers, rotamers, atropisomers or mixtures thereof.

Among the compounds which are the subject of the invention, there may be mentioned a second group of compounds of general formula (I), in which $Ar_1$ represents
an aryl group, in particular a phenyl, optionally substituted with one or more groups chosen independently of each other from the following groups: a halogen atom, a $(C_1\text{-}C_4)$alkyl group and a $(C_1\text{-}C_4)$alkoxy group;
a heterocyclyl group, in particular pyridinyl or pyrimidinyl, said heterocyclyl group being optionally substituted with one or more groups chosen independently of each other from the following groups: a halogen atom, a $(C_1\text{-}C_4)$alkyl group and a $(C_1\text{-}C_4)$alkoxy group;

T represents
a group —$(CH_2)_n$— with n=1;

$Ar_2$ represents
an aryl group, in particular a phenyl, optionally substituted with one or more groups chosen independently of each other from the following groups: a halogen atom, a $(C_1\text{-}C_4)$alkyl group and a $(C_1\text{-}C_4)$alkoxy group;
a heterocyclyl group, in particular pyridinyl, optionally substituted with one or more groups chosen independently of each other from the following groups: a halogen atom, a $(C_1\text{-}C_4)$alkyl group and a $(C_1\text{-}C_4)$alkoxy group;

$Ar_3$ represents
an aryl group, in particular a phenyl, optionally substituted with one or more groups chosen independently of each other from the following groups: a halogen atom, a hydroxyl group, a $(C_1\text{-}C_4)$alkyl group and a $(C_1\text{-}C_4)$alkoxy group;
a heterocyclyl group, in particular pyridinyl or furanyl, optionally substituted with one or more groups chosen independently of each other from the following groups: a hydroxyl group, a $(C_1\text{-}C_4)$alkyl group and a $(C_1\text{-}C_4)$alkoxy group;

$R_1$ represents a saturated heterocyclyl group of formula (A) in which:
$R_2$, $R_3$ and $R_4$ each represent a hydrogen atom or a $(C_1\text{-}C_4)$ alkyl group;
p=2; m=n=1; or
m=0; n=1; p=2; or
m=0; n=p=1; or
m=n=p=1;
or alternatively $R_1$ represents a cycloalkyl group of formula (B) in which:
$R_5$, $R_6$ and $R_7$ represent independently of each other a hydrogen atom or a $C_1\text{-}C_3$ alkyl group;
$R_8$ and $R_9$ represent independently of each other a hydrogen atom or a $C_1\text{-}C_3$ alkyl group;
n'=0 or 1; p'=1, 2 or 3;
in the form of a base, an addition salt with an acid, a hydrate or a solvate, in the form of enantiomers, diastereoisomers, rotamers, atropisomers or mixtures thereof.

Among the compounds which are the subject of the invention, there may be mentioned a third group of compounds of general formula (I), in which $Ar_1$ represents
a phenyl group, optionally substituted with one or more groups chosen independently of each other from the following groups: a halogen atom, a $(C_1\text{-}C_4)$ alkyl group and a $(C_1\text{-}C_4)$alkoxy group;
a pyridinyl or pyrimidinyl group, said pyridinyl and pyrimidinyl groups being optionally substituted with one or more groups chosen independently of each other from the following groups: a halogen atom and a $(C_1\text{-}C_4)$ alkyl group;

T represents
a group —$(CH_2)_n$— with n=1

$Ar_2$ represents
a phenyl group optionally substituted with one or more groups chosen independently of each other from the following groups: a halogen atom, a $(C_1-C_4)$alkyl group and a $(C_1-C_4)$alkoxy group;

a pyridinyl group, optionally substituted with one or more groups chosen independently of each other from the following groups: a halogen atom, a $(C_1-C_4)$alkyl group and a $(C_1-C_4)$alkoxy group;

$Ar_3$ represents a phenyl group optionally substituted with one or more groups chosen independently of each other from the following groups: a halogen atom, a hydroxyl group, a $(C_1-C_4)$alkyl group and a $(C_1-C_4)$alkoxy group;

a pyridinyl, furanyl or pyrazolyl group, said groups optionally substituted with one or more groups chosen independently of each other from the following groups: a hydroxyl group, a $(C_1-C_4)$alkyl group and a $(C_1-C_4)$alkoxy group;

$R_1$ represents a saturated heterocyclyl group of formula (A) in which:

$R_2$, $R_3$ and $R_4$ each represent a hydrogen atom and m=0; n=1; p=2;

or alternatively $R_1$ represents a cycloalkyl group of formula (B) in which:

$R_5$, $R_6$, $R_7$, $R_8$ and $R_9$ each represent a hydrogen atom;

n'=0 or 1 and p'=1, 2 or 3;

in the form of a base, an addition salt with an acid, a hydrate or a solvate, in the form of enantiomers, diastereoisomers, rotamers, atropisomers and mixtures thereof.

Among the compounds which are the subject of the invention, there may be mentioned a fourth group of compounds of general formula (I), in which $Ar_1$ represents a phenyl group, optionally substituted with one or more groups chosen independently of each other from the following groups: a halogen atom, a $(C_1-C_4)$alkyl group and a $(C_1-C_4)$alkoxy group;

a pyridinyl or pyrimidinyl group, said pyridinyl and pyrimidinyl groups being optionally substituted with one or more groups chosen independently of each other from the following groups: a halogen atom and a $(C_1-C_4)$ alkyl group;

T represents a group $-(CH_2)_n-$ with n=1

$Ar_2$ represents a phenyl group optionally substituted with one or more groups chosen independently of each other from the following groups: a halogen atom, a $(C_1-C_4)$alkyl group and a $(C_1-C_4)$alkoxy group;

a pyridinyl group, optionally substituted with one or more groups chosen independently of each other from the following groups: a halogen atom, a $(C_1-C_4)$alkyl group and a $(C_1-C_4)$alkoxy group;

$Ar_3$ represents a phenyl group optionally substituted with one or more groups chosen independently of each other from the following groups: a halogen atom, a hydroxyl group, a $(C_1-C_4)$alkyl group and a $(C_1-C_4)$alkoxy group;

a pyridinyl or furanyl group, said groups optionally substituted with one or more groups chosen independently of each other from the following groups: a hydroxyl group, a $(C_1-C_4)$alkyl group and a $(C_1-C_4)$ alkoxy group;

$R_1$ represents a saturated heterocyclyl group of formula (A) in which:

$R_2$, $R_3$ and $R_4$ each represent a hydrogen atom and m=0; n=1; p=2;

or alternatively $R_1$ represents a cycloalkyl group of formula (B) in which:

$R_5$, $R_6$, $R_7$, $R_8$ and $R_9$ each represent a hydrogen atom;

n'=0 or 1 and p'=1, 2 or 3;

in the form of a base, an addition salt with an acid, a hydrate or a solvate, in the form of enantiomers, diastereoisomers, rotamers, atropisomers or mixtures thereof.

Among the compounds which are the subject of the invention, there may be mentioned a fifth group of compounds of general formula (I), in which $Ar_1$ represents a phenyl group, optionally substituted with one or more groups chosen independently of each other from the following groups: a halogen atom, a $(C_1-C_4)$alkyl group and a $(C_1-C_4)$alkoxy group;

a pyridinyl group;

T represents a group $-(CH_2)_n-$ with n=1

$Ar_2$ represents a phenyl group optionally substituted with one or more groups chosen independently of each other from the following groups: a halogen atom, a $(C_1-C_4)$ alkyl group and a $(C_1-C_4)$alkoxy group;

$Ar_3$ represents a phenyl group optionally substituted with one or more groups chosen independently of each other from the following groups: a halogen atom, a hydroxyl group, a $(C_1-C_4)$alkyl group and a $(C_1-C_4)$alkoxy group;

$R_1$ represents a saturated heterocyclyl group of formula (A) in which:

$R_2$, $R_3$ and $R_4$ each represent a hydrogen atom; m=0; n=1 and p=2, or alternatively $R_1$ represents a cycloalkyl group of formula (B) in which:

$R_5$, $R_6$, $R_7$, $R_8$ and $R_9$ represent independently of each other a hydrogen atom; n'=0 and p'=3; in the form of a base, an addition salt with an acid, a hydrate or a solvate, in the form of enantiomers, diastereoisomers, rotamers, atropisomers or mixtures thereof.

Among the compounds which are the subject of the invention, there may be mentioned a sixth group of compounds of general formula (I), chosen from:

N-[4-chloro-2-(2,6-difluorobenzyl)phenyl]-3,4-dimethoxy-N-[(3S)-pyrrolidin-3-yl]benzenesulfonamide hydrochloride (compound No. 1);

N-[4-chloro-2-(2,6-difluorobenzyl)phenyl]-3,4-dimethoxy-N-piperidin-4-ylbenzenesulfonamide hydrochloride (compound No. 2);

N-[4-chloro-2-(2,5-difluorobenzyl)phenyl]-3,4-dimethoxy-N-pyrrolidin-3-ylbenzenesulfonamide hydrochloride (compound No. 3);

N-[4-chloro-2-(2,6-difluorobenzyl)phenyl]-3,4-dimethoxy-N-[(3R)-pyrrolidin-3-yl]benzenesulfonamide hydrochloride (compound No. 4);

N-azetidin-3-yl-N-[4-chloro-2-(2,6-difluorobenzyl)-phenyl]-3,4-dimethoxybenzenesulfonamide hydrochloride (compound No. 5);

Atropisomer $A_1$ of N-[2-(2,6-difluorobenzyl)-6-methoxyphenyl]-3,4-dimethoxy-N-[(3S)-pyrrolidin-3-yl]benzenesulfonamide hydrochloride (compound No. 6);

Atropisomer $B_1$ of N-[2-(2,6-difluorobenzyl)-6-methoxyphenyl]-3,4-dimethoxy-N-[(3S)-pyrrolidin-3-yl]benzenesulfonamide hydrochloride (compound No. 7);

N-[(1R,2S)-2-aminocyclopentyl]-N-[2-(2,6-difluorobenzyl)-6-methoxyphenyl]-3,4-dimethoxybenzene-sulfonamide hydrochloride (compound No. 8);

N-[4-chloro-2-(pyridin-2-ylmethyl)phenyl]-3,4-dimethoxy-N-[(3S)-pyrrolidin-3-yl]benzenesulfonamide hydrochloride (compound No. 9);

N-[4-chloro-2-(pyridin-2-ylmethyl)phenyl]-3,4-dimethoxy-N-[(3R)-pyrrolidin-3-yl]benzenesulfonamide hydrochloride (compound No. 10);

Atropisomer $A_2$ of N-[2-(2-chlorobenzyl)-6-methoxyphenyl]-3,4-dimethoxy-N-[(3S)-pyrrolidin-3-yl]benzenesulfonamide hydrochloride (compound No. 11);

Atropisomer $B_2$ of N-[2-(2-chlorobenzyl)-6-methoxyphenyl]-3,4-dimethoxy-N-[(3S)-pyrrolidin-3-yl]benzenesulfonamide hydrochloride (compound No. 12);

N-[[2-(2,6-difluorobenzyl)-5-methoxyphenyl]-3,4-dimethoxy-N-[(3S)-pyrrolidin-3-yl]benzenesulfonamide hydrochloride (compound No. 13);

Atropisomer $A_3$ of N-[(1S,2S)-2-aminocyclopentyl]-N-[2-(2,6-difluorobenzyl)-6-methoxyphenyl]-3,4-dimethoxy-benzenesulfonamide hydrochloride (compound No. 14);

Atropisomer $B_3$ of N-[(1S,2S)-2-aminocyclopentyl]-N-[2-(2,6-difluorobenzyl)-6-methoxyphenyl]-3,4-dimethoxy-benzenesulfonamide hydrochloride (compound No. 15);

N-[4-chloro-2-(2,6-difluorobenzyl)phenyl]-3-fluoro-4-methyl-N-[(3R)-pyrrolidin-3-yl]benzenesulfonamide hydrochloride (compound No. 16);

N-[4-chloro-2-(2,6-difluorobenzyl)phenyl]-3-fluoro-4-methyl-N-[(3S)-pyrrolidin-3-yl]benzenesulfonamide hydrochloride (compound No. 17);

Atropisomer $A_4$ of N-[2-(2,6-difluorobenzyl)-4-chloro-6-methoxyphenyl]-3,4-dimethoxy-N-[(3S)-pyrrolidin-3-yl]benzenesulfonamide hydrochloride (compound No. 18);

Atropisomer $B_4$ of N-[2-(2,6-difluorobenzyl)-4-chloro-6-methoxyphenyl]-3,4-dimethoxy-N-[(3S)-pyrrolidin-3-yl]benzenesulfonamide hydrochloride (compound No. 19);

Atropisomer $A_5$ of N-[2-(2,6-difluorobenzyl)-6-methoxyphenyl]-3-fluoro-4-methyl-N-[(3S)-pyrrolidin-3-yl]benzenesulfonamide hydrochloride (compound No. 20);

Atropisomer $B_5$ of N-[2-(2,6-difluorobenzyl)-6-methoxyphenyl]-3-fluoro-4-methyl-N-[(3S)-pyrrolidin-3-yl]benzenesulfonamide hydrochloride (compound No. 21);

N-[2-(2,6-difluorobenzyl)-4-methylphenyl]-3,4-difluoro-N-[(3S)-pyrrolidin-3-yl]benzenesulfonamide trifluoroacetate (compound No. 22);

N-[4-(2,6-difluorobenzyl)phenyl]-1,3,5-trimethyl-N-[(3S)-pyrrolidin-3-yl]-1H-pyrazole-4-sulfonamide hydrochloride (compound 23).

Among the compounds which are the subject of the invention, there may be mentioned a seventh group of compounds of the general formula (I), chosen from:

N-[4-chloro-2-(2,6-difluorobenzyl)phenyl]-3,4-dimethoxy-N-[(3S)-pyrrolidin-3-yl]benzenesulfonamide hydrochloride (compound No. 1);

Atropisomer $A_1$ of N-[2-(2,6-difluorobenzyl)-6-methoxyphenyl]-3,4-dimethoxy-N-[(3S)-pyrrolidin-3-yl]benzenesulfonamide hydrochloride (compound No. 6);

N-[(1R,2S)-2-aminocyclopentyl]-N-[2-(2,6-difluorobenzyl)-6-methoxyphenyl]-3,4-dimethoxy-benzenesulfonamide hydrochloride (compound No. 8);

Atropisomer $A_2$ of N-[2-(2-chlorobenzyl)-6-methoxyphenyl]-3,4-dimethoxy-N-[(3S)-pyrrolidin-3-yl]benzenesulfonamide hydrochloride (compound No. 11);

Atropisomer $A_3$ of N-[(1S,2S)-2-aminocyclopentyl]-N-[2-(2,6-difluorobenzyl)-6-methoxyphenyl]-3,4-dimethoxy-benzenesulfonamide hydrochloride (compound No. 14);

Atropisomer $A_4$ of N-[2-(2,6-difluorobenzyl)-4-chloro-6-methoxyphenyl]-3,4-dimethoxy-N-[(3S)-pyrrolidin-3-yl]benzenesulfonamide hydrochloride (compound No. 18).

When $Ar_2$ is an optionally substituted phenyl group, the T-$Ar_2$ bonds, on the one hand, and the $Ar_2$-N bonds, on the other hand, are in the ortho position. In other words, the nitrogen atom and the substituent T are on two adjacent carbon atoms.

In the context of the invention, a ($C_1$-$C_4$)alkyl group is understood to mean: a linear or branched saturated aliphatic group comprising from 1 to 4 carbon atoms, such as methyl, ethyl, propyl, isopropyl, butyl, isobutyl, sec-butyl or tert-butyl;

an optionally substituted ($C_1$-$C_4$)alkyl group is understood to mean: an alkyl group as defined above in which one or more hydrogen atoms have been substituted with a substituent;

a ($C_1$-$C_4$)alkoxy group is understood to mean: a ($C_1$-$C_4$)alkyl-O— radical where the ($C_1$-$C_4$)alkyl group is as defined above, for example methoxy, ethoxy, propoxy, isopropoxy, butoxy, isobutoxy, sec-butoxy or tert-butoxy;

a halogen atom is understood to mean: a fluorine atom, a chlorine atom, a bromine atom or an iodine atom;

a cycloalkyl group is understood to mean: a saturated cyclic alkyl group comprising from 3 to 8 carbon atoms, for example cyclopropyl, cyclobutyl, cyclopentyl or cyclohexyl. The cycloalkyl group may be optionally substituted with a ($C_1$-$C_4$)alkyl group, for example methylcyclopropyl, dimethylcyclopropyl, methylcyclobutyl, methylcyclopentyl, methylcyclohexyl, dimethyl-cyclohexyl, cycloheptyl or cyclooctyl;

an aryl group is understood to mean: a monocyclic or bicyclic aromatic group comprising between 6 and 10 carbon atoms, for example phenyl or naphthyl. The aryl group may be optionally substituted with 1, 2, 3 or 4 substituents;

a heterocyclyl group is understood to mean: a saturated, unsaturated or aromatic monocyclic group comprising between 4 and 7 atoms and comprising from 1 to 2 heteroatoms chosen from nitrogen, oxygen or sulfur. By way of example, there may be mentioned azetidine, piperidinyl, pyrrolidinyl, 1,3-dioxolanyl, imidazolyl, pyrazolyl, pyridinyl, thiazolyl, thienyl, pyrimidinyl or furanyl;

an aralkyl group is understood to mean: an alkyl chain substituted with an aryl group, such as for example a benzyl group;

an oxo group is understood to mean: a group of formula:

for example a group $R_1$ which represents a saturated heterocyclyl group of formula (A) in which:

$R_2$, $R_3$ and $R_4$ each represent a hydrogen atom; p=2 and m=n=1, is a piperidinyl group; or $R_2$, $R_3$ and $R_4$ each represent a hydrogen atom; m=0; n=1 and p=2, is a pyrrolidinyl group;

$R_2$, $R_3$ and $R_4$ each represent a hydrogen atom; m=0 and n=p=1, is an azetidine group;

for example, a group $R_1$ which represents a cycloalkyl group of formula (B) in which:

$R_5$, $R_6$, $R_7$, $R_8$ and $R_9$ each represent a hydrogen atom, p'=3 and n'=0, is a cyclopentyl group.

The compounds of general formula (I) may contain one or more asymmetric carbons. They can therefore exist in the form of enantiomers or diastereoisomers. These enantiomers and diastereoisomers, and mixtures thereof, including the racemic mixtures, form part of the invention.

By virtue of their structure, the compounds of general formula (I) may also be in the form of rotamers. In the context of the invention, the expression rotamers is understood to mean compounds which have identical structural formulae but different rigid spatial conformations. These differences in the rigid spatial conformations of these compounds can therefore confer different physicochemical properties on them and, even in some cases, different biological activities.

The compounds of general formula (I) may also exist in the form of atropisomers. The atropisomers are compounds with identical structural formulae, but which have a particular spatial configuration resulting from a restricted rotation around a single bond, due to a major steric hindrance on either side of this single bond. Atropisomerism is independent of the presence of stereogenic elements, such as an asymmetric carbon.

The compounds of formula (I) may exist in the form of bases or of addition salts with acids. Such addition salts form part of the invention. These salts are advantageously prepared with pharmaceutically acceptable acids, but the salts of other acids useful, for example, for the purification or separation of the compounds of general formula (I) also form part of the invention.

The compounds of general formula (I) may additionally be in the form of hydrates or solvates, namely in the form of associations or combinations with one or more molecules of water or with a solvent. Such hydrates and solvates also form part of the invention.

The subject of the present invention is also the method for preparing the compounds of general formula (I).

Accordingly, the compounds of general formula (I) may be prepared by the method illustrated in scheme 1. According to this scheme, the compounds of formula (I) may be obtained by a Mitsunobu reaction between the alcohols of formula (X) and the compounds of general formula (II).

In the compounds of formula (II), and (X), $Ar_1$, $Ar_2$, $Ar_3$, T and $R_1$ are as defined in formula (I).

In the Mitsunobu reaction, diisopropyl azodicarboxylate (DIAD) may be replaced by its analogs such as diethyl azodicarboxylate and di-tert-butyl azodicarboxylate, and triphenylphosphine may be grafted onto a resin (R. G. Gentiles et al., J. Comb. Chem. 2002, 4, 442-456).

The compounds of formula (I), for which $T=\!\!=\!\!(CH_2)_n\!\!-\!\!$ with n=1, may in some cases be obtained from the compounds having the structure (I), for which $T=\!\!=\!\!CH(R)\!\!-\!\!$ in which R represents a hydroxyl group, by the action of a hydride, for example triethylsilane, in the presence of boron trifluoride etherate.

The compounds of formula (I), for which

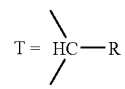

in which R represents a hydroxyl group, may, in some cases, be obtained from the corresponding ketone:

by the action of a hydride, for example sodium borohydride.

The compounds of formula (II) are obtained beforehand according to scheme 2, by sulfonylation of the compound of formula (III) with sulfonyl chlorides of formula (V) in the presence of a base chosen from tertiary amines such as pyridine according to the method described by Stauffer et al., Bioorg. Med. Chem. 2000, EN 8, 6, 1293-1316. As tertiary amines, triethylamine or diisopropylethylamine may also be used.

In some cases, it is possible to even envisage using a mixture of tertiary amines. The compounds of formula (V) are commercially available or may be obtained by adaptation of

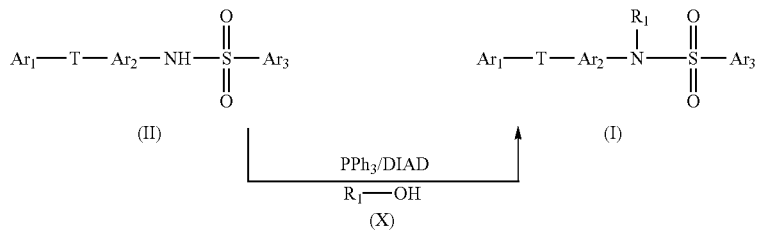

Scheme 1

The compounds of formula (I) for which $R_4$ is a hydrogen and $R_6$ and $R_7$ are hydrogens are obtained from compounds for which $R_4$ and $R_6$ are protecting groups, for example a tert-butoxycarbonyl (BOC).

the methods described, for example, by A. J. Prinsen et al., Recl. Trav. Chim. The Netherlands 1965, EN 84, 24.

In the compounds of formula (III) and (V), $Ar_1$, $Ar_2$, $Ar_3$ and T are as defined in formula (I).

Scheme 2

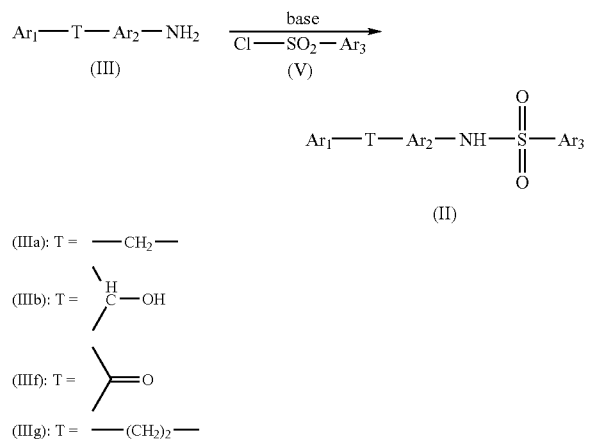

(IIIa): T = —CH$_2$—

(IIIb): T = $\overset{H}{\underset{}{\text{C}}}$—OH (IIIf): T = $=$O (IIIg): T = —(CH$_2$)$_2$—

The compounds of formula (IIIa), (IIIb) and (IIIf) are prepared according to schemes 3 to 5. The 2-nitrobenzaldehyde

Scheme 3

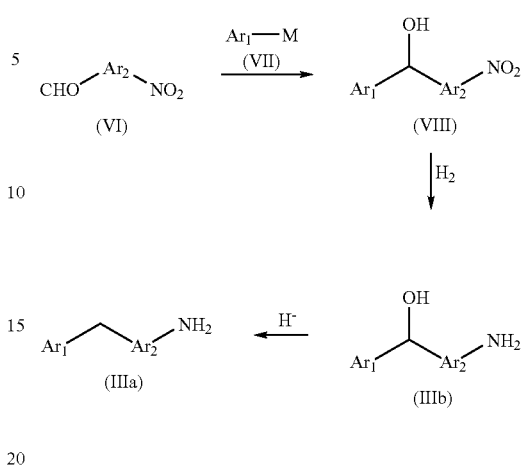

Other possibilities for synthesizing the compounds of general formulae (IIIb) and (IIIf) are presented in scheme 4.

Scheme 4

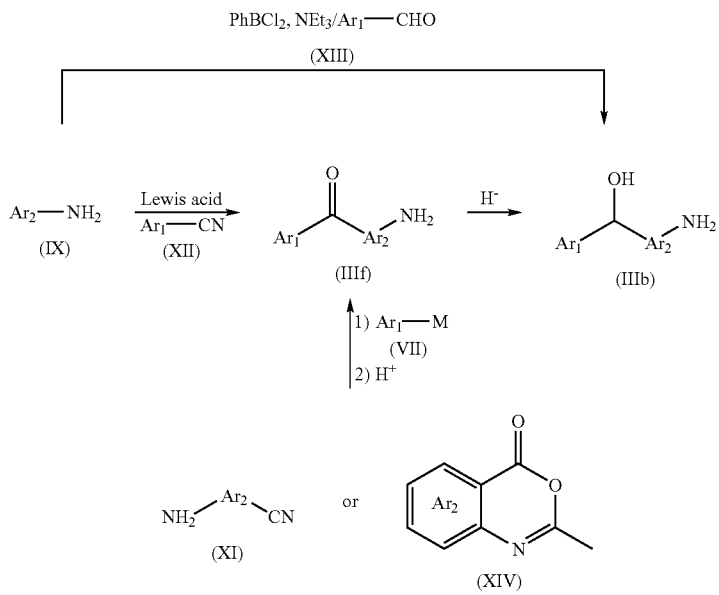

derivatives of formula (VI) react with organometallic compounds of formula (VII) in which M represents a group MgBr, MgI, ZnI or Li to give the compounds of formula (VIII). The organometallic compounds of formula (VII) are commercially available, or are formed according to conventional methods described in the literature. The nitro functional group of the compounds of formula (VIII) are reduced by hydrogenation, for example under the action of metal tin and of concentrated hydrochloric acid in ethanol, to give the compounds of formula (IIIb). The derivatives of formula (IIIb) are reduced by the action of hydrides, for example with a mixture of triethylsilane and trifluoroacetic acid in dichloromethane to give the derivatives of formula (IIIa).

The nitrobenzaldehydes of formula (VI) are commercially available or may be prepared, for example, according to an adaptation of the method described by J. Kenneth Horner et al., J. Med. Chem., 1968, 11; 5; 946.

The anilines of formula (IX) are condensed with benzonitriles of formula (XII), in the presence of a Lewis acid such as for example boron trichloride with aluminum trichloride or with gallium trichloride to give the compounds of formula (IIIf), according to the method described by T. Sugasawa et al. J.A.C.S. 1978; 100; 4842. The compounds of formula (IIIf) may be obtained by condensation of aminobenzonitriles (XI) with the organometallic derivatives (VII), according to the method described by R. Fryer et al., J. Heterocycl. Chem. 1991, EN 28; 7, 1661. The compounds of formula (IIIf) may also be obtained from the intermediate (XIV) according to an adaptation of the method described by D. Lednicer, J. Heterocyclic. Chem. 1971; 903.

The carbonyl functional group of the compounds (IIIf) is reduced by the action of a hydride, for example sodium borohydride in ethanol, to give the compounds of formula (IIIb).

Another method for preparing the compounds of formula (IIIb) consists in condensing anilines of formula (IX) with benzaldehyde derivatives of formula (XIII) in the presence of phenyldichloroborane and triethylamine according to the method described by T. Toyoda et al., Tet. Lett, 1980, 21, 173.

It should be noted that the compounds of formula (IIIf) under the action of triethylsilane and trifluoroacetic acid for example can lead to the compounds of formula (IIIa).

Another possibility for synthesizing the compounds of general formulae (IIIa), in which Ar₁ represents a heteroaryl, is presented in scheme 5.

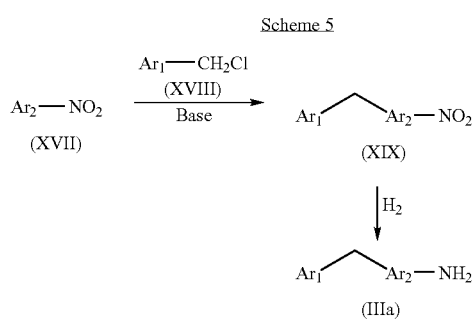

The nitrophenyls of formula (XVII) are condensed with aromatic chloromethylheterocyclyl in the presence of a base, for example potassium tert-butoxide, to give the derivatives (XIX) according to the method described by Florio. S et al., Eur. J. Org. Chem. 2004, 2118, which are reduced for example by the action of metal tin in the presence of 12M hydrochloric acid, to give the derivatives of formula (IIIa).

The compounds of formula (IIIg) are prepared according to scheme 6. The nitrobenzaldehydes (VI), by condensation with the derivatives (XV) according to a Wittig reaction, lead to the compounds (XVI). These derivatives are reduced for example by catalytic hydrogenation with palladium to give the compounds of formula (IIIg).

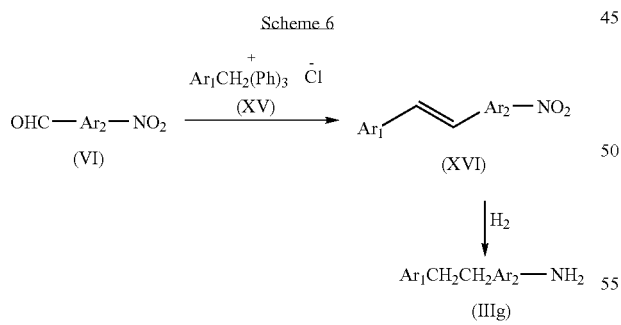

In all the schemes and for all the compounds of formulae (II) to (XIX), the meanings of $Ar_1$, T, $Ar_2$, $Ar_3$, $R_1$ are as defined for the compounds of general formula (I).

In schemes 1 to 6, the starting compounds and the reagents, when their mode of preparation is not described, are commercially available or are described in the literature, or alternatively may be prepared by methods which are described therein or which are known to persons skilled in the art.

When a compound contains a reactive functional group, for example a hydroxyl group, it may require prior protection before reaction. Persons skilled in the art will be able to determine the need for prior protection.

The compounds of formula (II) to (XIX) are useful as synthesis intermediates for the preparation of the compounds of general formula (I) and form an integral part of the present invention.

EXAMPLES

The following examples describe the preparation of the compounds in accordance with the invention. These examples are not limiting and merely illustrate the invention.

The exemplified compound numbers refer to those given in the table. Elemental microanalyses, mass spectra and NMR spectra confirm the structures of the compounds obtained.

The conditions for analysis by mass spectrometry coupled liquid chromatography LC/MS are the following:

for the liquid chromatography part: symmetry column C18 (2.1×50 mm) 3-5 µm. Eluent A=H₂O+0.005% of TFA, pH=3.14; eluent B=CH₃CN+0.005% of TFA, with a gradient from 100% of A to 90% of B over 10 minutes, and then 5 minutes at 90% of B for the mass spectrometry part: positive electrospray ionization mode.

When the ¹H NMR spectrum identifies rotamers, only the interpretation corresponding to the predominant rotamer is described.

In the following tables:
m.p.(° C.) represents the melting point of the compound in degrees Celsius
MH⁺ represents the mass peak of the ionized product
the retention time is expressed in minutes
n.d. means "not determined"
Me=methyl Example 1

N-[2-(2,6-Difluorobenzyl)-6-methoxyphenyl]-3,4-dimethoxy-N-[(3S)-pyrrolidin-3-yl]benzene-sulfonamide hydrochloride (compound 6)

Example 1.1

(2,6-Difluorophenyl)(3-methoxy-2-nitrophenyl)methanol 77.5 ml of a 1.6M solution of n-butyllithium (1.5 eq.) in hexane are added dropwise in order to maintain a temperature of less than or equal to −70° C. to a solution of 12.3 ml of 1,3-difluorobenzene (1.5 eq.) in 150 ml of tetrahydrofuran over 1 hour. After an additional 1 hour at −70° C., a solution of 15 g of 2-nitro-3-methoxybenzaldehyde in tetrahydrofuran is added over 1 hour still at −70° C. The reaction medium is stirred for 4 hours at −70° C. and then brought to a temperature of −5° C. over 1 hour. The reaction medium is then diluted by adding diethyl ether and then slowly hydrolyzed with a saturated aqueous solution of ammonium chloride. After decantation, the organic phase is washed with water and then dried over anhydrous sodium sulfate. The residue is chromatographed on silica gel, eluting with a dichloromethane/cyclohexane mixture (1/1) (v/v) in order to obtain 13.4 g of the expected product.

$^1$H NMR δ in ppm (DMSO d 6): 3.85 (s, 3H); 6.16 (t, 1H); 6.53 (d, 1H); 7.00-7.61 (unresolved complex, 6H).

Example 1.2

(2-Amino-3-methoxyphenyl)(2,6-difluorophenyl) methanol 13.3 g of (2,6-difluorophenyl)(3-methoxy-2-nitro-phenyl) methanol are dissolved in 75 ml of ethanol. At 0° C., 37 ml of concentrated hydrochloric acid (10 eq.) are slowly added to 10.5 g of tin (2.2 eq.) (exothermic reaction). After 18 hours, the ethanol is evaporated, the residue is taken up in ethyl acetate before being alkalinized with a 3N aqueous sodium hydroxide solution until the pH is close to 14. After decantation, the organic phase is dried over anhydrous sodium sulfate and concentrated in order to obtain 8.7 of the expected product.

$^1$H NMR δ in ppm (DMSO d 6): 3.79 (s, 3H); 4.48 (s, 2H); 5.98 (t, 1H) 6.07 (d, 1H); 6.52-7.43 (unresolved complex, 6H).

Example 1.3

2-(2,6-Difluorobenzyl)-6-methoxyaniline

The reaction mixture composed of 5.8 g of (2-amino-3-methoxyphenyl)(2,6-difluorophenyl)methanol, 11 ml of triethylsilane (3 eq.), 10 ml of trifluoroacetic acid (3.9 eq.) in 90 ml of dichloromethane is heated for 6 hours at 40° C. After one night at room temperature, the reaction medium is slowly hydrolyzed in the cold state with 6N sodium hydroxide, the organic phase is dried over anhydrous sodium sulfate and concentrated. The residue is purified by filtration on silica H, eluting with dichloromethane, in order to obtain 3.8 g of the expected product.

$^1$H NMR δ in ppm (DMSO d 6): 3.77 (s, 5H); 4.65 (s, 2H); 6.15 (d, 1H) 6.45 (t, 1H); 6.70 (d, 1H); 7.12-7.46 (unresolved complex, 3H).

Example 1.4

N-[2-(2,6-Difluorobenzyl)-6-methoxyphenyl]-3,4-dimethoxybenzene-sulfonamide 3.8 g of 2-(2,6-difluorobenzyl)-6-methoxyaniline are dissolved in 36 ml of tetrahydrofuran and 1.2 ml of pyridine, and then 4.06 g of 3,4-dimethoxybenzene-sulfonyl chloride are then added. After 18 hours at room temperature, the reaction medium is taken up in ethyl acetate and then hydrolyzed, the organic phase is dried over anhydrous sodium sulfate and concentrated. The residue is solidified in a toluene/ethyl acetate mixture (9/1) (v/v) in order to obtain 5 g of expected product.

$^1$H NMR δ in ppm (DMSO d 6): 3.17 (s, 3H); 3.75 (s, 3H); 3.83 (s, 3H) 4.22 (s, 2H); 6.37 (d, 1H); 6.75 (d, 1H); 7.02-7.43 (unresolved complex, 7H); 9.16 (s, 1H).

Example 1.5 tert-Butyl (3S)-3-{[6-methoxy-2-(2,6-difluorophenyl][(3,4-dimethoxy-phenyl)sulfonyl] amino}pyrrolidine-1-carboxylate 1.55 g of di-tert-butyl azodicarboxylate are added at room temperature to 2.8 g of triphenylphosphine in solution in 25 ml of tetrahydrofuran. After 30 minutes, 0.95 g of tert-butyl (3R)-3-hydroxypyrrolidine-1-carboxylate is introduced. After 30 minutes, 1.46 g of N-[2-(2,6-difluorobenzyl)-6-methoxyphenyl]-3,4-dimethoxybenzenesulfonamide are added and the mixture is left for 48 hours at room temperature. The reaction medium is concentrated and chromatographed on silica gel in order to obtain 0.44 g of the first atropisomer and 0.42 g of the second atropisomer.

Example 1.6

N-[2-(2,6-Difluorobenzyl)-6-methoxyphenyl]-3,4-dimethoxy-N-[(3S)-pyrrolidin-3-yl]benzenesulfonamide hydrochloride 7 ml of a 2M hydrogen chloride solution in diethyl ether are added to 0.44 g of the first atropisomer tert-butyl (3S)-3-{[6-methoxy-2-(2,6-difluorophenyl]-[(3,4-dimethoxyphenyl) sulfonyl]amino}pyrrolidine-1-carboxylate in ethyl acetate. After 18 hours at room temperature, the medium is filtered and the precipitate is taken up in a dichloromethane/ethyl acetate mixture at 70° C. The insoluble material is filtered in order to obtain 0.084 g of the expected product.

$^1$H NMR δ in ppm (DMSO d 6): 1.76 (m, 1H); 2.43 (m, 1H) 2.80 (t, 1H); 3.17 (m, 3H); 3.38 (s, 3H); 3.80 (s, 3H); 3.84 (s, 3H); 4.05 (q, 2H); 4.72 (q, 1H); 6.36 (d, 1H); 6.95 (d, 1H); 7.14-7.53 (unresolved complex, 7H); 9.19 (s, 2H).

m.p.=254° C.

The terms "atropisomer $A_n$" or "atropisomer $B_n$" are used in order to be able to clearly name two atropisomers of the same pair.

In the text that follows, the melting points were determined with the apparatus:

(M)=Metler Toledo, (K)=Kofler stage

In table I which follows, the compounds are in the monohydrochloride form

TABLE I
(Ia)
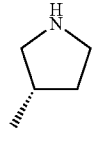
| Compound No. | Nature and position of the substituents | | | | m.p. (°C.) | MH+/retention time |
|---|---|---|---|---|---|---|
| | on Ar₁ | on Ar₂ | R₁ | on Ar₃ | | |
| 1 | 2,6-diF | 4-Cl | 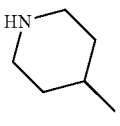 | 3,4-diOMe | 199 (M) | 523/7.00 |
| 2 | 2,6-diF | 4-Cl | 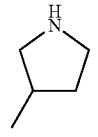 | 3,4-diOMe | 185.5 (M) | 537/6.41 |
| 3 | 2,5-diF | 4-Cl | 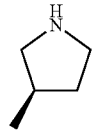 | 3,4-diOMe | 122 (M) | 523/7.02 |
| 4 | 2,6-diF | 4-Cl | 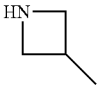 | 3,4-diOMe | 197.9 (M) | 523/6.93 |
| 5 | 2,6-dIF | 4-Cl | 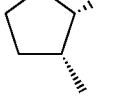 | 3,4-diOMe | 171.8 (M) | 509/6.91 |
| 8 | 2,6-diF | 6-OMe | 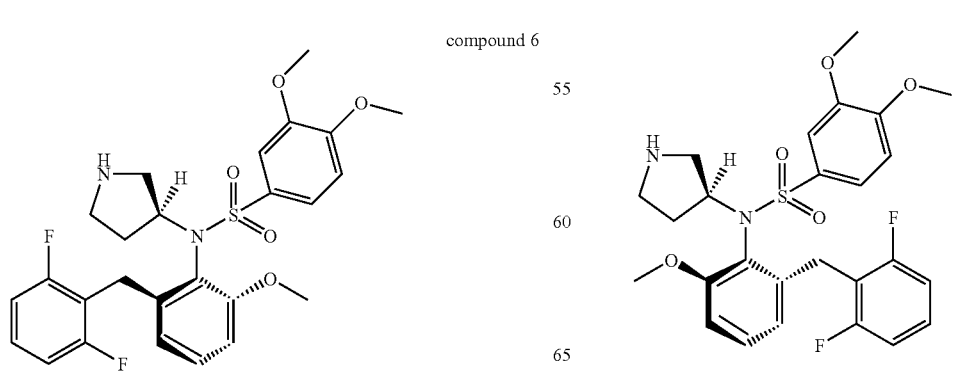 | 3,4-diOMe | 138.2 (M) | 488.1/5.64 |
Compounds 6 and 7 form a pair of atropisomers.
compound 6
compound 7

For Compound 6 (Atropisomer $A_1$):
  m.p.=129° C. (M)
  $(\alpha_D)$=+54.3 at c=0.35 g/dl in methanol
  MH$^+$/retention time: 519.2/6.56
For Compound 7 (Atropisomer $B_1$):
  m.p.=254° C. (M)
  $\alpha_D$=−25.95 at c=0.42 g/dl in methanol
  MH$^+$/retention time: 519.2/6.56

Other compounds of formula (Ia) are given by way of example in table I' below. These compounds are in the monohydrochloride form.

The pairs of compounds which follow form pairs of atropisomers:

compounds 11 and 12,
compounds 14 and 15,
compounds 18 and 19,
compounds 20 and 21.

Compound 22 in table I'' which follows is in the trifluoroacetate form:

TABLE I'

| Compound No. | on $Ar_1$ | on $Ar_2$ | $R_1$ | on $Ar_3$ | m.p. (° C.) | MH$^+$/retention time |
|---|---|---|---|---|---|---|
| 11 (atropisomer $A_2$) | 2-Cl | 6-OMe | pyrrolidine | 3,4-diOMe | 231 (M) | 517/6.78 |
| 12 (atropisomer $B_2$) | 2-Cl | 6-OMe | pyrrolidine | 3,4-diOMe | 160.9 (M) | 517/6.67 |
| 13 | 2,6-diF | 5-OMe | pyrrolidine | 3,4-diOMe | 136.4 (M) | 519/670 |
| 14 (atropisomer $A_3$) | 2,6-diF | 6-OMe | cyclopentyl-NH$_2$/Me | 3,4-diOMe | 156 (K) | 533/6.70 |
| 15 (atropisomer $A_3$) | 2,6-diF | 6-OMe | cyclopentyl-NH$_2$/Me | 3,4-diOMe | 156 (K) | 533/6.87 |
| 16 (R) | 2,6-diF | 4-Cl | pyrrolidine | 3-F 4-Me | 148 (K) | 495/7.48 |
| 17 (S) | 2,6-diF | 4-Cl | pyrrolidine | 3-F 4-Me | 145 (K) | 495/7.45 |
| 18 (atropisomer $A_4$) | 2,6-diF | 4-Cl 6-OMe | pyrrolidine | 3,4-diOMe | 262.8 (M) | 553/6.96 |
| 19 (atropisomer $B_4$) | 2,6-diF | 4-Cl 6-OMe | pyrrolidine | 3,4-diOMe | 202 (M) | 553/7.00 |
| 20 (atropisomer $A_5$) | 2,6-diF | 6-OMe | pyrrolidine | 3-F 4-Me | 110 (K) | 491/6.65 |
| 21 (atropisomer $B_5$) | 2,6-dIF | 6-OMe | pyrrolidine | 3-F 4-Me | 122 (K) | 491/6.71 |

TABLE I"

| Compound No. | Nature and position of the substituents | | | | m.p. (° C.) | MH+/retention time |
|---|---|---|---|---|---|---|
| | on Ar₁ | on Ar₂ | R₁ | on Ar₃ | | |
| 22 | 2.6-diF | 4-Me | HN–(pyrrolidinyl with methyl) | 3.4-diF | 97.9 (M) | 479/7.29 |

Example 2

N-[4-Chloro-2-(pyridin-2-ylmethyl)phenyl]-3,4-dimethoxy-N-[(3S)-pyrrolidinyl-3-yl]benzene-sulfonamide hydrochloride (compound No. 10)

Example 2.1

2-(5-Chloro-2-nitrobenzyl)pyridine 8.66 g of 4-chloronitrobenzene and 8.2 g of 2-chloromethylpyridine in solution in 100 ml of dimethyl sulfoxide are slowly added to 22.44 g of potassium tert-butoxide in 500 ml of dimethyl sulfoxide. After 18 hours at room temperature, the mixture is hydrolyzed with a saturated ammonium chloride solution and extracted three times with dichloromethane. The organic phase is dried over anhydrous sodium sulfate and concentrated. The residue is filtered on silica H (eluent dichloromethane) in order to obtain 10.695 g of the expected product.

¹H NMR δ in ppm (DMSO d 6): 4.49 (s, 2H); 7.20-7.31 (unresolved complex, 2H); 7.60-7.78 (unresolved complex, 3H); 8.03 (d, 1H); 8.41 (d, 1H)

m.p.=69° C.

Example 2.2

4-Chloro-2-pyridin-2-ylmethyl)aniline 4.7 g of metal tin and then 16.8 ml of 12M hydrochloric acid are successively added at room temperature to 5 g of 2-(5-chloro-2-nitrobenzyl)pyridine in solution in 34 ml of ethanol. After 2 hours at room temperature, the medium is neutralized at 0° C. by the addition of 6M sodium hydroxide. The reaction medium is extracted with ethyl acetate, the organic phase is dried over anhydrous sodium sulfate and concentrated in order to obtain 3.86 g of the expected product.

¹H NMR δ in ppm (DMSO d 6): 3.93 (s, 2H); 5.33 (s, 2H); 6.66 (d, 1H); 6.93-7.06 (unresolved complex, 2H); 7.21-7.38 (unresolved complex, 2H); 7.76 (m, 1H); 8.47 (d, 1H)

Example 2.3

N-[4-Chloro-2-(pyridin-2-ylmethyl)-phenyl]-3,4-dimethoxybenzenesulfonamide 0.7 ml of pyridine and then 2.27 g of 3,4-dimethoxybenzenesulfonyl chloride are successively added at room temperature to 1.86 g of 4-chloro-2-(pyridin-2-ylmethyl)aniline in solution in 20 ml of tetrahydrofuran. After 72 hours at room temperature, the reaction medium is taken up in water and extracted with ethyl acetate, the organic phase is dried over anhydrous sodium sulfate and concentrated in order to obtain 2.12 g of the expected product.

¹H NMR δ in ppm (DMSO d 6): 3.71 (s, 3H); 3.83 (s, 3H); 3.94 (s, 2H); 7.07-7.32 (unresolved complex, 8H); 7.74 (m, 1H); 8.54 (d, 1H)

Example 2.4 tert-Butyl (3R)-3-{[4-chloro-2-(pyridin-ylmethyl)phenyl][(3,4-dimethoxyphenyl)-sulfonyl]amino}pyrrolidine-1-carboxylate 0.91 ml of diisopropylazodicarboxylate is added at room temperature to 1.21 g of triphenylphosphine in solution in 25 ml of tetrahydrofuran. After 30 minutes, 0.86 g of tert-butyl (3S)-3-hydroxypyrrolidine-1-carboxylate is introduced. After 30 minutes, 1.29 g of N-[4-chloro-2-(pyridin-2-ylmethyl)phenyl]-3,4-dimethoxybenzene-sulfonamide are added and the mixture is left for 18 hours at room temperature. The reaction medium is concentrated and chromatographed on silica gel in order to obtain 2.94 g of the expected product.

¹H NMR δ in ppm (DMSO d 6): 1.36 (s, 9H); 1.6 (m, 1H); 2.15 (m, 1H); 2.8-3.1 (unresolved complex, 3H); 3.6 (m, 1H); 3.78 (s, 3H); 3.88 (s, 3H); 4.2-4.6 (unresolved complex, 3H); 7.09-7.75 (unresolved complex, 10H).

Example 2.5

N-[4-Chloro-2-(pyridin-2-ylmethyl)-phenyl]-3,4-dimethoxy-N-[(3R)-pyrrolidinyl-3-yl]-benzene-sulfonamide hydrochloride 2.8 ml of a 2M hydrogen chloride solution in diethyl ether are added to 2.94 g of tert-butyl (3R)-3-{[4-chloro-2-(pyridin-ylmethyl)phenyl][(3,4-dimethoxy-phenyl)sulfonyl]amino}pyrrolidine-1-carboxylate in 3 ml of ethyl acetate. After 18 hours at room temperature, the reaction medium is concentrated and the residue is solidified with diethyl ether in order to obtain, after drying, 0.921 g of the expected product.

¹H NMR δ in ppm (DMSO d 6): 1.38 (m, 1H); 1.76 (m, 1H); 3.0-3.3 (unresolved complex, 4H); 3.79 (s, 3H); 3.88 (s, 3H); 4.55-4.88 (unresolved complex, 3H); 6.60-8.50 (unresolved complex, 10H); 14.1 (s, 1H).

m.p.=138.2° C.

In table II which follows, the compounds are in the monohydrochloride form.

TABLE II (Ib)

TABLE II-continued

| Compound No. | Nature and position of the substituents | | | | m.p. (° C.) | MH+/ retention time |
|---|---|---|---|---|---|---|
| | on Ar₁ | on Ar₂ | R₁ | on Ar₃ | | |
| 9 (S) | H | 4-Cl | (S)-3-pyrrolidinyl | 3,4-diOMe | 138.2 (M) | 488/5.71 |
| 10 (R) | H | 4-Cl | (R)-3-pyrrolidinyl | 3,4-diOMe | 203.4 (M) | 488/5.73 |

In table III which follows, the compound is in the monohydrochloride form.

TABLE III (Ib)

| Compound No. | Nature and position of the substituents | | | | m.p. (° C.) | MH+/retention time |
|---|---|---|---|---|---|---|
| | on Ar₁ | on Ar₂ | R₁ | on Ar₃ | | |
| 23 | 2,6-diF | 4-Cl | trans-4-Me-pyrrolidin-3-yl | N-1-Me 3-Me 5-Me | 144.6 (M) | 495/6.60 |

Pharmacological Testing

The compounds of the invention were the subject of pharmacological studies which showed their importance as active substances in therapy.

They were in particular tested for their effects. More particularly, the affinity of the compounds of the invention for the orexin 2 receptors was determined in an in vitro binding test according to the technique described below. This method consists in studying the displacement of radioiodinated orexin A attached to the human orexin 2 receptors expressed in CHO cells. The test is performed on membranes in a 50 mM Hepes incubation buffer containing 1 mM $MgCl_2$, 25 mM $CaCl_2$, 0.025% $NaN_3$, 1% bovine serum albumin (BSA) and 100 pM of ligand for 30 minutes at 25° C. The reaction is stopped by filtration and washing on a Whatman GF/C filter. The nonspecific binding is measured in the presence of $10^{-6}$M human orexin B. The $IC_{50}$ values (concentration inhibiting 50% of the binding of radioiodinated orexin A to its receptors) are low, less than 300 nM, in particular less than 100 nM and more particularly less than 30 nM.

The affinity of the compounds according to the invention for the orexin 1 receptors was also studied in an in vitro binding test according to the same technique using radioiodinated orexin A as ligand in a membrane preparation of CHO cells expressing the human orexin 1 receptors. The compounds according to the invention have little or no affinity for the orexin 1 receptors.

The agonist or antagonist character of the compounds is determined in vitro for the test for measuring intracellular calcium (FLIPR) on a cellular preparation expressing the orexin 2 receptors according to the general technique described in Sullivan et al., Methods Mol. Biol., 1999, Vol. 114, 125-133, using 1 μM of Fluo-4 AM as fluorescent calcium indicator. For the antagonist test, the compounds are preincubated for 30 minutes before adding 0.25 nM of orexin B. The $IC_{50}$ values for the orexin 2 receptors measured in these studies are low and more particularly less than 100 nM.

The $IC_{50}$ values were measured for the compounds according to the invention (compound Nos. 1, 6, 8, 11, 14 and 18). The data which follow serve to illustrate the invention and are not limiting.

TABLE 1

| Compound No. | $IC_{50}$ OX 2 (nM) |
|---|---|
| 6 | 9.1 |
| 8 | 11 |
| 11 | 7.2 |
| 14 | 10 |
| 18 | 12 |

The following table illustrates the affinity of a few compounds according to the invention for the orexin 1 and 2 receptors, in an in vitro binding test according to the technique described above.

TABLE 2

| Compound No. | $IC_{50}$ OX 2 (nM) | $IC_{50}$ OX 1 (nM) |
|---|---|---|
| 1 | 16.4 | 1380 |
| 7 | 9 | 103 |

The biological results show that the compounds according to the invention are indeed specific antagonists for the orexin 2 receptors.

Their antagonist character is determined in vitro in a test for measuring intracellular calcium (FLIPR) according to the general technique mentioned above.

Accordingly, the compounds of the present invention, as antagonists for the orexin 2 receptors, may be used in the prophylaxis and treatment of any diseases involved in a dysfunction linked to these receptors.

The compounds of the invention may be used for the preparation of a medicament intended for the prophylaxis or for the treatment of any diseases involving a dysfunction linked to the orexin 2 receptor, and more particularly in the prophylaxis or the treatment of pathologies in which an orexin 2 receptor antagonist provides a therapeutic benefit. Such pathologies are for example obesity, appetite or taste disruptions including cachexia, anorexia, bulimia (Smart et al., Eur. J. Pharmacol., 2002, 440, 2-3, 199-212), diabetes (Ouedraogo et al., Diabetes, 2002, 52, 111-117), metabolic syndromes (Sakurai, Curr. Opin. Nutr. Metab. Care, 2003, 6, 353-360), vomiting and nausea (U.S. Pat. No. 6,506,774), depression and anxiety (Salomon et al., Biol. Psychiatry, 2003, 54, 96-104; Jaszberenyi et al., J. Neuroendocrinol., 2000, 12, 1174-1178), epilepsy (Morales et al. Brain Res., 2006, 1109, 164-175), addictions (Georgescu et al., J. Neurosci., 2003, 23, 8, 3106-3111; Kane et al., Endocrinology, 2000, 141, 10, 3623-3629), mood and behavioral disorders, schizophrenia (Nishino et al., Psychiatry Res., 2002, 110, 1-7), sleep disorders (Sakurai, Neuroreport, 2002, 13, 8, 987-995), restless leg disease (Allen et al., Neurology, 2002, 59, 4, 639-641), learning and memory disorders (van den Pol et al., 2002, J. Physiol., 541(1), 169-185; Jaeger et al., Peptides, 2003, 23, 1683-1688; Telegdy and Adamik, Regul. Pept., 2002, 104, 105-110), sexual and psychosexual dysfunctions (Gulia et al., Neuroscience, 2003, 116, 921-923), pain, visceral or neuropathic pain, hyperalgesia, allodynia (U.S. Pat. No. 6,506,774; Suyama et al., In vivo, 2004, 18, 2, 119-123), digestive disorders (Takakashi et al., Biochem. biophy. Res. Comm., 1999, 254, 623-627; Matsuo et al., Eur. J. Pharmacol., 2002, 105-109), irritable bowel syndrome (U.S. Pat. No. 6,506,774), neuronal degeneration (van den Pol, Neuron, 2000, 27, 415-418), ischemic or hemorrhagic strokes (Irving et al., Neurosci. Lett., 2002, 324, 53-56), Cushing's disease, Guillain-Barré syndrome (Kanbayashi et al., Psychiatry Clin. Neurosci., 2002, 56, 3, 273-274), myotonic dystrophy (Martinez-Rodriguez et al., Sleep, 2003, 26, 3, 287-290), urinary incontinence (Blackstone et al., AGS Annual Meeting, poster P491,2002), hyperthyroidism (Malendowicz et al., Biomed. Res., 2001, 22, 5, 229-233), pituitary function disorders (Voisin et al., Cell. Mol. Life. Sci., 2003, 60, 72-78), hypertension or hypotension (Samson et al. Brain Res., 1999, 831, 1-2, 248-253).

The use of the compounds according to the invention for the preparation of a medicament intended for the prevention or treatment of the above-mentioned pathologies forms an integral part of the invention.

The subject of the invention is also medicaments which comprise a compound of formula (I). These medicaments find use in therapy, in particular in the prophylaxis or treatment of the abovementioned pathologies.

According to another of its aspects, the present invention relates to pharmaceutical compositions containing, as active ingredient, at least one compound according to the invention. These pharmaceutical compositions contain an effective dose of a compound according to the invention and optionally one or more pharmaceutically acceptable excipients.

Said excipients are chosen according to the pharmaceutical dosage form and the desired mode of administration among the customary excipients which are known to persons skilled in the art.

In the pharmaceutical compositions of the present invention for oral, sublingual, subcutaneous, intramuscular, intravenous, topical, local, intratracheal, intranasal, transdermal or rectal administration, the active ingredient of formula (I) above, or its potential salt, solvate or hydrate, may be administered in a unit form for administration, as a mixture with conventional pharmaceutical excipients, to animals and to human beings for the prophylaxis or the treatment of the above disorders or diseases.

The appropriate unit forms for administration comprise the oral forms such as tablets, soft or hard gelatin capsules, powders, granules, chewing gums and oral solutions or suspensions, the forms for sublingual, buccal, intratracheal, intraocular or intranasal administration, or the forms for administration by inhalation, the forms for subcutaneous, intramuscular or intravenous administration and the forms for rectal or vaginal administration. For topical application, the compounds according to the invention may be used in creams, ointments or lotions.

For example, when a solid composition is prepared in the form of tablets, the main active ingredient is mixed with a pharmaceutical excipient, such as gelatin, starch, lactose, magnesium stearate, talc, gum arabic or the like. The tablets may be coated with sucrose, a cellulose derivative or other materials. The tablets may also be made by various techniques, direct compression, dry granulation, wet granulation or hot melt.

In order to obtain the desired prophylactic or therapeutic effect, the dose of active ingredient may vary between 0.1 and 200 mg per kg of body weight and per day. Although these dosages are examples of an average situation, there may be specific cases where higher or lower dosages are appropriate, such dosages also belong to the invention. According to the usual practice, the dosage appropriate for each patient is determined by the doctor according to the mode of administration, the weight and the response of said patient.

Each unit dose may contain from 0.1 to 1000 mg, preferably from 0.1 to 500 mg, of active ingredient in combination with one or more pharmaceutical excipients. This unit dose may be administered 1 to 5 times per day so as to administer a daily dosage of 0.5 to 5000 mg, preferably of 0.5 to 2500 mg.

The present invention, according to another of its aspects, also relates to a method for the prevention or treatment of the pathologies indicated above, which comprises the administration of a compound according to the invention, of a pharmaceutically acceptable salt, of a solvate or of a hydrate of said compound.

We claim:

1. A compound of formula (I):

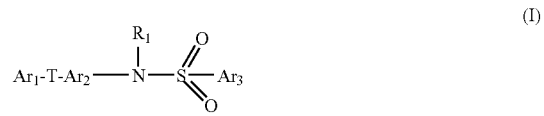

wherein:

Ar$_1$ is an aryl group or a heterocyclyl group, each of which is optionally substituted with one or more groups chosen independently of each other from a halogen atom, a (C$_1$-C$_4$)alkyl group and a (C$_1$-C$_4$)alkoxy group;

T is —(CH$_2$)$_n$—, wherein n is 0, 1, 2; or a group:

wherein R is a hydroxyl group;

$Ar_2$ is an aryl group or a heterocyclyl group, each of which is optionally substituted with one or more groups chosen independently of each other from a halogen atom, a $(C_1-C_4)$alkyl group and a $(C_1-C_4)$alkoxy group;

$Ar_3$ is an aryl group, optionally substituted with one or more groups chosen independently of each other from a halogen atom, a hydroxyl group, a $C_1-C_4)$alkyl group and a $(C_1-C_4)$alkoxy group; or
 a heterocyclyl group, optionally substituted with one or more groups chosen independently of each other from a hydroxyl group, a $(C_1-C_4)$alkyl group and a $(C_1-C_4)$ alkoxy group; and $R_1$ is a saturated heterocyclyl group of formula (A):

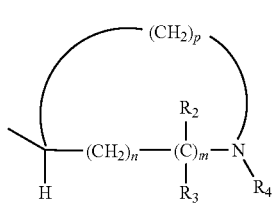

(A)

wherein:
$R_2$ and $R_3$ are independently of each other a hydrogen atom, or a $C_1-C_4$ alkyl group; or
$R_2$ and $R_3$ form together an oxo group;
$R_4$ is a hydrogen atom or a $C_1-C_3$ alkyl group;
n is 0 or 1;
m is 0 or 1; and
p is 1 or 2;
provided that m and n are not both 0 at the same time; or
a cycloalkyl group of formula (B):

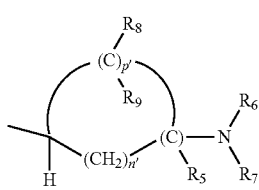

(B)

wherein:
$R_5$, $R_6$ and $R_7$ are independently of each other a hydrogen atom or a $C_1-C_3$ alkyl group;
$R_8$ and $R_9$ are independently of each other a hydrogen atom or a $C_1-C_3$ alkyl group; or
$R_8$ and $R_9$ form together an oxo group;
n' is 0, 1 or 2; and
p' is 1, 2, 3 or 4;

or an addition salt with an acid thereof, or an enantiomer, diastereoisomer, rotamer, atropisomer thereof or a mixture thereof.

2. The compound according to claim 1, wherein:
T is —$CH_2$—; and
$R_1$ is a saturated heterocyclyl group of formula (A), wherein:
$R_2$, $R_3$ and $R_4$ each are a hydrogen atom or a $C_1-C_4$)alkyl group; and
p is 2; and m and n are both 1; or
m is 0; n is 1; and p is 2; or
m is 0; and n and p are both 1; or
m, n, p are all 1; or
a cycloalkyl group of formula (B) wherein:
$R_5$, $R_6$ and $R_7$ are independently of each other a hydrogen atom or a $C_1-C_3$ alkyl group;
$R_8$ and $R_9$ are independently of each other a hydrogen atom or a $C_1-C_3$ alkyl group;
n' =0, 1; and
p' =1,2 or 3;
or an addition salt with an acid thereof, or an enantiomer, diastereoisomer, rotamer, atropisomer thereof or a mixture thereof.

3. The compound according to claim 1, wherein:
$Ar_1$ is a phenyl group, optionally substituted with one or more groups chosen independently of each other from a halogen atom, a $(C_1-C_4)$alkyl group and a $(C_1-C_4)$ alkoxy group; or
a pyridinyl or pyrimidinyl group, each of which is optionally substituted with one or more groups chosen independently of each other from a halogen atom and a $(C_1-C_4)$alkyl group;
T is —$CH_2$—;
$Ar_2$ is a phenyl or pyridinyl group, each of which is optionally substituted with one or more groups chosen independently of each other from a halogen atom, a $(C_1-C_4)$ alkyl group and a $(C_1-C_4)$alkoxy group;
$Ar_3$ is a phenyl group optionally substituted with one or more groups chosen independently of each other from a halogen atom, a hydroxyl group, a $(C_i-C_4)$alkyl group and a $(C_i-C_4)$alkoxy group; or
a pyridinyl, furanyl or pyrazolyl group, each of which is optionally substituted with one or more groups chosen independently of each other from a hydroxyl group, a $C_1-C_4)$alkyl group and a $(C_1-C_4)$alkoxy group; and
$R_1$ is a saturated heterocyclyl group of formula (A) wherein:
$R_2$, $R_3$ and $R_4$ each are a hydrogen atom;
m is 0;
n is 1; and
p is 2; or
a cycloalkyl group of formula (B) wherein:
$R_5$, $R_6$, $R_7$, $R_8$ and $R_9$ each are a hydrogen atom;
n' is 0 or 1; and
p' is 1,2 or 3;
or an addition salt with an acid thereof, or an enantiomer, diastereoisomer, rotamer, atropisomer thereof or a mixture thereof.

4. The compound according to claim 3, wherein:
$Ar_3$ is a phenyl group optionally substituted with one or more groups chosen independently of each other from a halogen atom, a hydroxyl group, a $C_1-C_4)$alkyl group and a $(C_1-C_4)$alkoxy group; or
a pyridinyl or furanyl group, each of which is optionally substituted with one or more groups chosen independently of each other from a hydroxyl group, a $(C_1-C_4)$ alkyl group and a $(C_1-C_4)$alkoxy group;
or an addition salt with an acid thereof, or an enantiomer, diastereoisomer, rotamer, atropisomer thereof or a mixture thereof.

5. The compound according to claim 3, wherein:
Ar$_1$ is a phenyl group, optionally substituted with one or more groups chosen independently of each other from a halogen atom, a (C$_1$-C$_4$)alkyl group and a (C$_1$-C$_4$) alkoxy group; or
a pyridinyl group;
Ar$_2$ is a phenyl group optionally substituted with one or more groups chosen independently of each other from a halogen atom, a (C$_1$-C$_4$)alkyl group and a (C$_1$-C$_4$) alkoxy group;
Ar$_3$ is a phenyl group optionally substituted with one or more groups chosen independently of each other from a halogen atom, a hydroxyl group, a (C$_1$-C$_4$)alkyl group and a (C$_1$-C$_4$)alkoxy group; and
R$_1$ is a saturated heterocyclyl group of formula (A) wherein:
R$_2$, R$_3$ and R$_4$ each are a hydrogen atom;
m =0;
n =1; and
p =2; or
a cycloalkyl group of formula (B) wherein:
R$_5$, R$_6$, R$_7$, R$_8$ and R$_9$ are independently of each other a hydrogen atom;
n' =0; and
p' =3;
or an addition salt with an acid thereof, or an enantiomer, diastereoisomer, rotamer, atropisomer thereof or a mixture thereof.

6. The compound according to claim 1, which is:
N-[4-chloro-2-(2,6-difluorobenzyl)phenyl]-3,4-dimethoxy-N-[(3S)-pyrrolidin-3-yl ]benzenesulfonamide hydrochloride;
N-[4-chloro-2-(2,6-difluorobenzyl)phenyl]-3,4-dimethoxy-N-piperidin-4-ylbenzenesulfonamide hydrochloride;
N-[4-chloro-2-(2,5-difluorobenzyl)phenyl]-3,4-dimethoxy-N-pyrrolidin-3-ylbenzenesulfonamide hydrochloride;
N-[4-chloro-2-(2,6-difluorobenzyl)phenyl]-3,4-dimethoxy-N-[(3R)-pyrrolidin-3-yl ]benzenesulfonamide hydrochloride;
N-azetidin-3yl-N-[4-chloro-2-(2,6-difluorobenzyl)phenyl]-3,4-dimethoxybenzenesulfonamide hydrochloride;
Atropisomer A$_l$ of N-[2-(2,6-difluorobenzyl)-6-methoxyphenyl]-3,4-dimethoxy-N-[(3S)-pyrrolidin -3-yl]benzenesulfonamide hydrochloride;
Atropisomer B$_1$ of N-[2-(2,6-difluorobenzyl)-6-methoxyphenyl]-3,4-dimethoxy-N-[(3S)-pyrrolidin -3-yl]benzenesulfonamide hydrochloride;
N-[(1R,2S)-2-aminocyclopentyl]-N-[2-(2,6-difluorobenzyl)-6-methoxyphenyl]-3,4-dimethoxybenzenesulfonamide hydrochloride;
N-[4-chloro-2-(pyridin-2-ylmethyl)phenyl]-3,4-dimethoxy-N-[(3S)-pyrrolidin-3-yl ]benzenesulfonamide hydrochloride;
N-[4-chloro-2-(pyridin-2-ylmethyl)phenyl]-3,4-dimethoxy-N-[(3R)-pyrrolidin-3-yl ]benzenesulfonamide hydrochloride;
Atropisomer A$_2$ of N-[2-(2-chlorobenzyl)-6-methoxyphenyl]-3 ,4-dimethoxy-N-[(3 S)-pyrrolidin-3-yl]benzenesulfonamide hydrochloride;
Atropisomer B$_2$ of N-[2-(2-chlorobenzyl)-6-methoxyphenyl]-3 ,4-dimethoxy-N-[(3 S)-pyrrolidin-3-yl]benzenesulfonamide hydrochloride;
N-[2-(2,6-difluorobenzyl)-5-methoxyphenyl]-3,4-dimethoxy-N-[(3S)-pyrrolidin-3-yl ]benzenesulfonamide hydrochloride;
Atropisomer A$_3$ of N-[(1 S,2S)-2-aminocyclopentyl]-N-[2-(2,6-difluorobenzyl)-6-methoxyphenyl ]-3,4-dimethoxybenzenesulfonamide hydrochloride;
Atropisomer B$_3$ of N-[(1S,2S)-2-aminocyclopentyl]-N-[2-(2,6-difluorobenzyl)-6-methoxyphenyl ]-3,4-dimethoxybenzenesulfonamide hydrochloride;
N-[4-chloro-2-(2,6-difluorobenzyl)phenyl]-3-fluoro-4-methyl-N-[(3R)-pyrrolidin-3-yl ]benzenesulfonamide hydrochloride;
N-[4-chloro-2-(2,6-difluorobenzyl)phenyl]-3-fluoro-4-methyl-N-[(3S)-pyrrolidin-3-yl ]benzenesulfonamide hydrochloride;
Atropisomer A$_4$ of N-[2-(2,6-difluorobenzyl)-4-chloro-6-methoxyphenyl]-3 ,4-dimethoxy-N-[(3S)-pyrrolidin-3-yl]benzenesulfonamide hydrochloride;
Atropisomer B$_4$ of N-[2-(2,6-difluorobenzyl)-4-chloro-6-methoxyphenyl]-3 ,4-dimethoxy-N-[(3S)-pyrrolidin-3-yl]benzenesulfonamide hydrochloride;
Atropisomer A$_5$ of N-[2(2,6-difluorobenzyl)-6-methoxyphenyl]-3-fluoro-4-methyl-N-[(3 S)-pyrrolidin -3-yl] benzenesulfonamide hydrochloride;
Atropisomer B$_5$ of N-[2-(2,6-difluorobenzyl)-6-methoxyphenyl]-3-fluoro-4-methyl-N-[(3 S)-pyrrolidin -3-yl] benzenesulfonamide hydrochloride;
N-[2-(2,6-difluorobenzyl)-4-methylphenyl]-3,4-difluoro-N-[(3S)-pyrrolidin-3-yl ]benzenesulfonamide trifluoroacetate; or
N-[4-(2,6-difluorobenzyl)phenyl]-1,3,5-trimethyl-N-[(3S)-pyrrolidin-3-yl]-1H-pyrazole-4-sulfonamide hydrochloride.

7. The compound according to claim 1, which is:
N-[4-chloro-2-(2,6-difluorobenzyl)phenyl]-3,4-dimethoxy-N-[(3S)-pyrrolidin-3-yl ]benzenesulfonamide hydrochloride;
Atropisomer A$_l$ of N-[2(2,6-difluorobenzyl)-6-methoxyphenyl]-3,4-dimethoxy-N-[(3S)-pyrrolidin -3-yl]benzenesulfonamide hydrochloride;
N-[(1R,2S)-2-aminocyclopentyl]-N-[2-(2,6-difluorobenzyl)-6-methoxyphenyl]-3,4-dimethoxy-benzenesulfonamide hydrochloride;
Atropisomer A$_2$ of N-[2-(2-chlorobenzyl)-6-methoxyphenyl]-3 ,4-dimethoxy-N-[(3 S)-pyrrolidin-3-yl]benzenesulfonamide hydrochloride;
Atropisomer A$_3$ of N-[(1S,2S)-2-aminocyclopentyl]-N-[2-(2,6-difluorobenzyl)-6-methoxyphenyl ]-3,4-dimethoxybenzenesulfonamide hydrochloride; or
Atropisomer A$_4$ of N-[2-(2,6-difluorobenzyl)-4-chloro-6-methoxyphenyl]-3 ,4-dimethoxy-N-[(3S)-pyrrolidin-3-yl]benzenesulfonamide hydrochloride.

8. A pharmaceutical composition comprising the compound according to claim 1, or an addition salt with an acid thereof, or an enantiomer, diastereoisomer, rotamer, atropisomer thereof or a mixture thereof, in combination with at least one pharmaceutically acceptable excipient.

9. A pharmaceutical composition comprising the compound according to claim 2, or an addition salt with an acid thereof, or an enantiomer, diastereoisomer, rotamer, atropisomer thereof or a mixture thereof, in combination with at least one pharmaceutically acceptable excipient.

10. A pharmaceutical composition comprising the compound according to claim 3, or an addition salt with an acid thereof, or an enantiomer, diastereoisomer, rotamer, atropisomer thereof or a mixture thereof, in combination with at least one pharmaceutically acceptable excipient.

11. A pharmaceutical composition comprising the compound according to claim 4, or an addition salt with an acid thereof, or an enantiomer, diastereoisomer, rotamer, atropisomer thereof or a mixture thereof, in combination with at least one pharmaceutically acceptable excipient.

12. A pharmaceutical composition comprising the compound according to claim 5, or an addition salt with an acid thereof, or an enantiomer, diastereoisomer, rotamer, atropisomer thereof or a mixture thereof, in combination with at least one pharmaceutically acceptable excipient.

13. A pharmaceutical composition comprising the compound according to claim 6, or an addition salt with an acid thereof, or an enantiomer, diastereoisomer, rotamer, atropisomer thereof or a mixture thereof, in combination with at least one pharmaceutically acceptable excipient.

14. A pharmaceutical composition comprising the compound according to claim 7, or an addition salt with an acid thereof, or an enantiomer, diastereoisomer, rotamer, atropisomer thereof or a mixture thereof, in combination with at least one pharmaceutically acceptable excipient.

* * * * *